US012583823B2

(12) United States Patent
Ren et al.

(10) Patent No.: US 12,583,823 B2
(45) Date of Patent: Mar. 24, 2026

(54) CRYSTAL FORM OF DAPRODUSTAT, PREPARATION METHOD THEREFOR AND USE THEREOF

(71) Applicant: Shenzhen Rentai Pharmatech Ltd., Shenzhen (CN)

(72) Inventors: Guobin Ren, Shenzhen (CN); Weijie Ji, Shenzhen (CN); Dongxu Yi, Shenzhen (CN); Jiajun Huang, Shenzhen (CN)

(73) Assignee: Shenzhen Jingtai Technology Co., LTD., Shenzhen (CN)

(*) Notice: Subject to any disclaimer, the term of this patent is extended or adjusted under 35 U.S.C. 154(b) by 1072 days.

(21) Appl. No.: 17/675,778

(22) Filed: Feb. 18, 2022

(65) Prior Publication Data

US 2022/0169619 A1 Jun. 2, 2022

Related U.S. Application Data

(63) Continuation of application No. PCT/CN2019/101496, filed on Aug. 20, 2019.

(51) Int. Cl.
*C07D 239/62* (2006.01)

(52) U.S. Cl.
CPC ........ *C07D 239/62* (2013.01); *C07B 2200/13* (2013.01)

(58) Field of Classification Search
CPC .......................... C07D 239/62; C07B 2200/13
See application file for complete search history.

(56) References Cited

U.S. PATENT DOCUMENTS 11,117,871 B2 9/2021 Chen et al.

FOREIGN PATENT DOCUMENTS

| | | | | |
|---|---|---|---|---|
| CN | 101505752 A | | 8/2009 | |
| WO | 2019052133 A1 | | 3/2019 | |
| WO | WO-2020102302 A1 | * | 5/2020 | ........... C07D 239/60 |

OTHER PUBLICATIONS

Yeh (Chem. Sci., 2017, 8, 7651-68). (Year: 2017).*
Chinese Office Action dated Feb. 25, 2023 regarding Chinese Application No. 201980002213.9 filed Aug. 20, 2019.
Japanese Office Action dated Mar. 8, 2018 regarding Japanese Application No. JP2018-35112 filed Mar. 8, 2018.
Becker KA, Jones JJ. An Emerging Treatment Alternative for Anemia in Chronic Kidney Disease Patients: A Review of Daprodustat. Adv Ther. Jan. 2018;35(1):5-11. doi: 10.1007/s12325-017-0655-z. Epub Dec. 28, 2017. PMID: 29285707; PMCID: PMC5778168.

(Continued)

*Primary Examiner* — Kortney L. Klinkel
*Assistant Examiner* — Richard Grant Peckham
(74) *Attorney, Agent, or Firm* — DINSMORE & SHOHL LLP

(57) ABSTRACT

Disclosed is crystal form M of the proline hydroxylase inhibitor daprodustat, wherein the X-ray powder diffraction thereof, expressed in 2θ angles and using Cu-Ka radiation, has characteristic peaks at 4.7±0.2°, 6.5±0.2°, and 6.8±0.2°. Disclosed are the preparation method for and the use of crystal form M. The crystal form M has good light stability, high temperature stability and high humidity stability, good solubility, and high purity.

18 Claims, 9 Drawing Sheets

(56) References Cited

OTHER PUBLICATIONS

International Search Report and Written Opinion mailed Jun. 20, 2020 in reference to co-pending Chinese Patent Application No. PCT/CN2019/101496 filed Aug. 20, 2019.
Yuan, "Clinical research progress of new chronic kidney disease anemia drugs", Chinese Journal of New Drugs, vol. 27, No. 17, Sep. 30, 2018.

* cited by examiner

CRYSTAL FORM OF DAPRODUSTAT, PREPARATION METHOD THEREFOR AND USE THEREOF

CROSS-REFERENCE TO RELATED APPLICATIONS

This application is a continuation application of International Patent Application No. PCT/CN2019/101496 with an international filing date of Aug. 20, 2019, designating the United States, now pending. The contents of the aforementioned application are incorporated herein by reference.

TECHNICAL FIELD

The present disclosure relates to the technical field of pharmaceutical crystals, in particular to a crystal form of a proline hydroxylase inhibitor, a preparation method therefor and use thereof.

BACKGROUND

N-[(1,3-dicyclohexylhexahydro-2,4,6-trioxo-5-pyrimidinyl)carbonyl]glycine of a formula (I) below, also known as Daprodustat, is a proline hydroxylase inhibitor developed by SmithKline Beecham P.L.C (GSK) that can inhibit proline hydroxylase and thereby promotes the production of red blood cells, and the red blood cells may carry oxygen to the parts of the body that need oxygen, thus achieve the purpose of relieving anemia. This is similar to the effects that occur in the body of humans in high altitude areas, and Daprodustat has shown good clinical efficacy in relieving anemia and safety and is more convenient for patients to take than an injection form of recombinant human erythropoietin for injection.

(I)

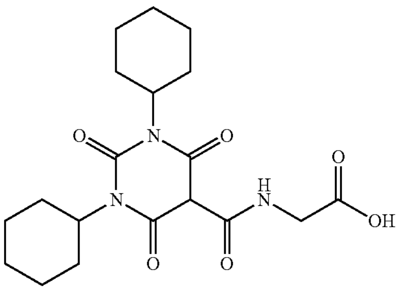

Patent document WO2019052133 discloses two crystal forms of a daprodustat compound (crystal forms CS1 and CS9). Although both crystal forms can significantly improve the purity of the compound compared with existing solid drugs, the dissolution performance of tablets prepared therefrom is not good due to poor solubility of the crystal forms. Good dissolution performance is a prerequisite for good bioavailability and is essential for druggability. Therefore, it is necessary to conduct polymorph screening in order to develop a new crystal form of the daprodustat compound with high purity and high solubility, making it more suitable for industrial production.

SUMMARY

Therefore, the technical problem to be solved by the present disclosure is to solve the problem of poor solubility and low purity of the existing proline hydroxylase inhibitor daprodustat.

In order to achieve the above purpose, the present inventors conducted careful research and discovered two new crystal forms of a proline hydroxylase inhibitor, named as a crystal form M and a crystal form K respectively. Wherein, the crystal form M has significantly improved solubility compared with the crystal form K and the existing crystal forms CS1 and CS9, and has higher purity and excellent stability, thus completing the present disclosure.

Specifically, the present disclosure involves the following technical solutions.

The disclosure provides a crystal form M of a proline hydroxylase inhibitor, wherein an X-ray powder diffraction of the crystal form M using Cu-Kα radiation has characteristic peaks at 2θ angles of 4.7±0.2°, 6.5±0.2° and 6.8±0.2°.

Further, the X-ray powder diffraction of the crystal form M using Cu-Kα radiation further has a characteristic peak at 2θ angle of 20.7±0.2°.

Further, the X-ray powder diffraction of the crystal form M using Cu-Kα radiation further has characteristic peaks at 2θ angles of 7.5±0.2° and 7.9±0.2°.

Further, the crystal form M has the following X-ray powder diffraction pattern data:

| 2θ (±0.2°) | d (Å) | I % |
|---|---|---|
| 4.7 | 18.9 | 27.7 |
| 6.5 | 13.7 | 15.7 |
| 6.8 | 13.0 | 100 |

Further, the crystal form M has the following X-ray powder diffraction pattern data:

| 2θ (±0.2°) | d (Å) | I % |
|---|---|---|
| 4.7 | 18.9 | 27.7 |
| 6.5 | 13.7 | 15.7 |
| 6.8 | 13.0 | 100 |
| 7.5 | 11.7 | 4.8 |
| 7.9 | 11.1 | 3.4 |

Further, the crystal form M has the following X-ray powder diffraction pattern data:

| 2θ (±0.2°) | d (Å) | I % |
|---|---|---|
| 4.68 | 18.88 | 27.7 |
| 6.45 | 13.69 | 15.7 |
| 6.81 | 12.97 | 100 |
| 7.55 | 11.70 | 4.8 |
| 7.95 | 11.11 | 3.4 |
| 10.77 | 8.21 | 1.6 |
| 15.27 | 5.80 | 3.5 |
| 16.63 | 5.33 | 1.6 |
| 17.49 | 5.07 | 1.5 |
| 20.67 | 4.30 | 9 |
| 21.67 | 4.09 | 2.2 |

Further, the crystal form M has an X-ray powder diffraction pattern substantially as shown in FIG. 1.

Further, a differential scanning calorimetry curve of the crystal form M has an absorption peak at 122.8±2° C.

Further, the crystal form M has a differential scanning calorimetry curve substantially as described in FIG. 2.

Further, the crystal form M has a thermal weight loss of less than 3.2% before 100° C. in a thermo gravimetric analysis curve.

Further, the crystal form M has a thermo gravimetric analysis curve substantially as shown in FIG. 3.

The present disclosure also provides a method for preparing the crystal form M of the proline hydroxylase inhibitor as described above, including the steps of dissolving a crystal form CS1 of the proline hydroxylase inhibitor in n-butanol or isobutanol, adding an aqueous solution of sodium dodecyl benzenesulfonate and concentrating to obtain a solid, adding the solid into water for slurrying, filtering and drying to obtain the crystal form M.

The present disclosure also provides a pharmaceutical composition, including the crystal form M as described above and a pharmaceutically acceptable excipient.

The present disclosure also provides use of a pharmaceutically effective amount of the crystal form M as described above or the pharmaceutical composition in the manufacture of a medicament for preventing or treating anemia, ischemia or myocardial infarction.

The present disclosure also provides a method for preventing or treating anemia, ischemia or myocardial infarction, including a step of administering a pharmaceutically effective dose of the pharmaceutical composition to a patient.

The technical solutions of the present disclosure have the following advantages:

The crystal form M and the crystal form K of the proline hydroxylase inhibitor provided by the present disclosure have higher purity, good light stability, high temperature stability and high humidity stability, and good solubility. The saturation solubility of the crystal form M is increased by 1.82 times, 1.73 times and 2.19 times compared with the crystal form K and the crystal forms CS9 and CS1 disclosed in the existing patents, respectively. The purity is higher, in which the purity of the crystal form M is 99.96%, the purity of the crystal form K is 99.91% and the purity of crystal form CS9 is 99.83%, and thus the purities of the crystal forms M and K are improved by 0.13% and 0.08%, respectively, compared with the crystal form CS9 disclosed in the existing patents. It is convenient to control the production conditions, and the method provided by the disclosure has simple preparation process, stable quality and easy for large-scale industrial production.

BRIEF DESCRIPTION OF THE DRAWINGS

In order to more clearly illustrate the technical solutions in the specific embodiments of the present disclosure or the prior art, the following is a brief description of accompanying drawings to be used in the specific embodiments or the prior art. It will be apparent that the accompanying drawings in the following description are some embodiments of the present disclosure and that other drawings may be obtained without creative effort by those of ordinary skill in the art based on these drawings.

DETAILED DESCRIPTION

Figure 1:
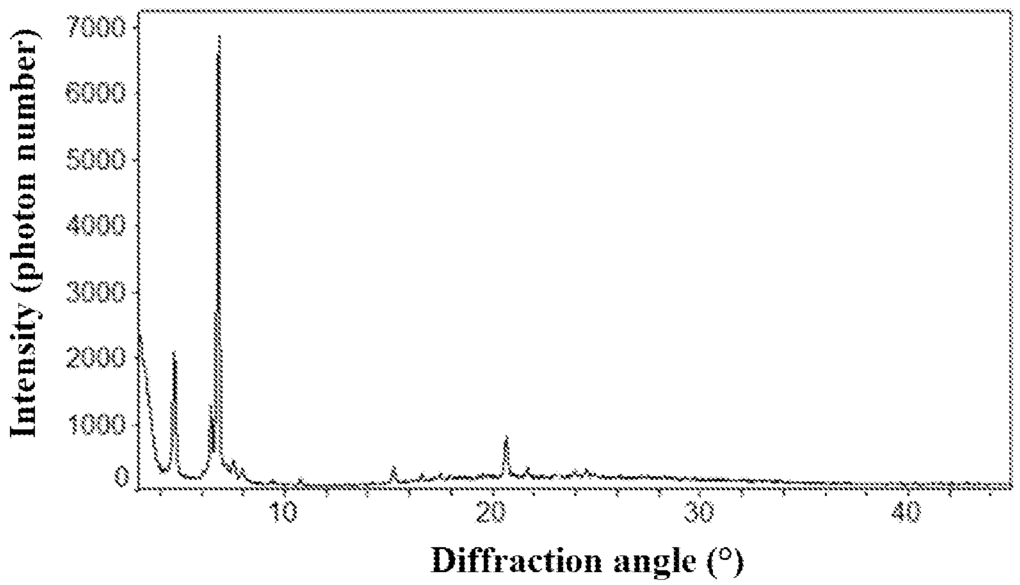
FIG. 1 is an X-ray diffraction pattern of a crystal form M in Example 1 according to the present disclosure.

In both the description and the claims of the present disclosure, compounds are named based on chemical structural formulae, and if a name of a compound is inconsistent with a chemical structural formula when a same compound is represented, the compound is named based on the chemical structural formula or a chemical reaction formula.

In the present application, scientific and technical terms used herein have the meanings commonly understood by those skilled in the art, unless otherwise stated. However, for a better understanding of the disclosure, definitions and explanations of some of relevant terms are provided below. In addition, where the definitions and explanations of the terms provided in this application are inconsistent with the meanings commonly understood by those skilled in the art, the meanings of the terms are based on the definitions and explanations of the terms provided in this application.

X-ray powder diffraction (XRPD) refers to that when an X-ray beam illuminates onto an object, the X-ray beam is scattered by atoms in the object, and each atom produces scattered waves that interfere with each other, resulting in diffraction. The result of the superposition of diffraction waves is that the intensity of the rays intensifies in some directions and decreases in other directions. A crystal structure can be obtained by analyzing the diffraction results. An X-ray diffractometer uses a diffraction principle to accurately determine the crystal structure, texture and stress of a substance, and to perform precise phase, qualitative and quantitative analyses. For crystalline materials, when the crystals to be measured are at different angles to an incident beam, those crystal planes that satisfy Bragg diffraction are detected, which are reflected in the XRPD pattern as diffraction peaks with different diffraction intensities. For amorphous materials, the XRPD patterns thereof are some diffuse scattering broad peaks because the structure does not have a long-range order of atomic arrangements in the crystal structure, but only a short-range order in the range of a few atoms.

The "2θ angle" mentioned in the present disclosure means that the X-ray diffraction analysis is based on a Bragg formula (the Bragg formula is $2d \sin \theta = n\lambda$), where "θ" refers to a glancing angle or Bragg angle, which is a complement angle of an angle of incidence. "2θ" refers to a diffraction angle; "d" refers to an interplanar distance between two adjacent crystal faces in a crystal lattice, with Å as a unit; "λ" refers to a wavelength of X-rays; "n" is any positive integer, and the X-ray diffraction is referred to as n-order diffraction accordingly. The horizontal coordinate corresponding to the powder diffraction peak in an XRPD pattern is the 2θ angle, and the error range of the 2θ angle at the peak position is ±0.3°, optionally ±0.2°. When the crystal form of the disclosure is determined by X diffraction, there is sometimes a slight error in the determination of peaks due to the instrument or conditions for measurement, so this error should be considered when determining the crystalline structure. Therefore, the applicant has considered the error range (±0.2) when determining the 2θ angle. "Substantially as shown in figure" means that at least 50%, or at least 60%, or at least 70%, or at least 80%, or at least 90%, or at least 99% of peaks are shown in the figure.

Differential scanning calorimetry (DSC) is a thermal analysis method. The power difference (e.g. in the form of heat) input to a sample and a reference as a function of temperature is measured at a program-controlled temperature. A curve recorded by a differential scanning calorimeter is called a DSC curve, which uses a rate of heat absorption or release of a sample, that is, a heat flow rate dH/dt (unit: mJ/sec) or heat flow (unit: W/g) as a vertical coordinate, and the temperature T or time t as a horizontal coordinate. The DSC curve can be used to determine a variety of thermodynamic and kinetic parameters, such as specific heat capacity, heat of reaction, heat of transformation, phase diagram, reaction rate, crystallization rate, polymer crystallinity and sample purity.

Thermogravimetric analysis (TGA) is a thermal analysis technique that measures the mass of a sample to be measured as a function of temperature at a program-controlled temperature to study the thermal stability and composition of a substance. A thermogravimetric method is to measure the mass of a substance as a function of temperature (or time) under a program-controlled temperature. The mass of the measured substance changes when the measured substance is subjected to sublimation, vaporization, decomposition into gases or loss of crystallization water during the heating process. At this time, the thermogravimetric curve is not straight but decreases somewhat. By analyzing the thermogravimetric curve, it is possible to know at what temperature the measured substance changes and to calculate how much material, such as crystallization water, is lost based on the weight loss. TGA experiments are useful for studying changes in the properties of crystals, for example, the physical phenomena of substances such as melting, evaporation, sublimation and adsorption, as well as the chemical phenomena of substances such as dissociation, oxidation, reduction, thermal stability, decomposition processes, quantitative analysis of ingredients, effects of additives and fillers, moisture and volatiles, and reaction kinetics. Thermogravimetric analysis is usually divided into two categories: dynamic (temperature rise) and static (constant temperature). The curve obtained by the thermogravimetric test is called a thermogravimetric curve (a TG curve). The TG curve is expressed in terms of mass as a vertical coordinate, and can also be expressed in other forms such as percent weight loss; temperature (or time) as a horizontal coordinate, with increase in temperature (or time) from left to right.

EXPERIMENTAL SOLUTION

The following examples are provided for a better understanding of the present disclosure, are not limited to the preferred embodiments and does not constitute a limitation on the content and protection scope of the disclosure. Any product identical or similar to the present disclosure, derived by anyone under the inspiration of the present disclosure or by combining the features in the present disclosure with that in the prior art, falls within the protection scope of the present disclosure.

Example 1 Preparation of a Crystal Form M 50 mg of a crystal form CS1 of a compound of a formula (I) was weighed in a sample vial, 10 ml of n-propanol was added, and the mixture was heated to 40° C. to completely dissolve the compound, then 100 μl of a 0.1 mol/L aqueous sodium dodecyl benzenesulfonate solution was added, and the mixture was stirred at 35° C. for 24 h, concentrated, and filtered to obtain a white solid precipitate. 5 ml of water was added to the white solid precipitate for slurrying, then another 5 ml of water was added, and the obtained solution was stirred for 2 h, filtered, and dried to obtain an off-white solid. XRPD test was performed on the off-white solid, showing a crystalline structure, named as a crystal form M. The structure of the crystal form M was characterized by differential scanning calorimetry (DSC) and thermogravimetric analysis (TGA), respectively.

(1) X-Ray Powder Diffraction (XRPD)

X-ray powder diffraction was performed by using the crystal form M, with the following measurement conditions:

determination was performed by using Cu-Kα under a voltage of 40 KV, and a current of 40 mA at a test angle of 3-45°, a step length of 0.02°, an exposure time of 0.2S, and a light tube slit width of 1 mm by using a Dtex detector with a slit width of 2.7 mm and a Germany BRUKER D8 DISCOVER type X-ray powder diffractometer.

An XRPD pattern of the above described crystal form M is shown in FIG. 1. An X-ray powder diffraction of the crystal form M has characteristic peaks at 2θ angles of 4.7±0.2°, 6.5±0.2° and 6.8±0.2°, also has a characteristic peak at 2θ angle of 20.7±0.2°, as well as also has characteristic peaks at 2θ angles of 7.5±0.2° and 7.9±0.2°. The specific peak positions of X-ray diffraction of the crystal form M are shown in Table 1.

TABLE 1

| X-ray diffraction results of the crystal form M | | |
|---|---|---|
| 2θ (±0.2°) | d (Å) | I % |
| 4.677 | 18.8789 | 27.7 |
| 6.451 | 13.6901 | 15.7 |
| 6.811 | 12.9667 | 100 |
| 7.549 | 11.7005 | 4.8 |
| 7.949 | 11.1126 | 3.4 |
| 10.768 | 8.2093 | 1.6 |
| 15.267 | 5.7986 | 3.5 |
| 16.625 | 5.3281 | 1.6 |
| 17.487 | 5.0674 | 1.5 |
| 20.661 | 4.2954 | 9 |
| 21.696 | 4.0928 | 2.2 |

(2) DSC Determination

DSC determination was performed by using the crystal form M under the following conditions:

determination was performed by a TA250 differential scanning calorimeter from TA Instrument Company, USA, with nitrogen protection and a heating rate of 10° C./min.

Figure 2:
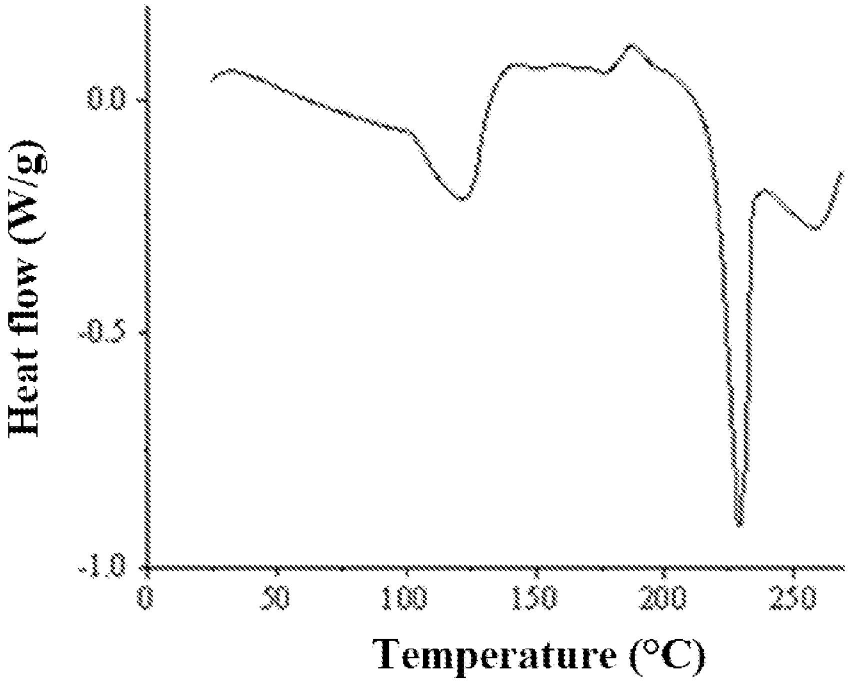
FIG. 2 is a differential scanning calorimetry curve of the crystal form M in Example 1 according to the present disclosure.

The DSC pattern of the crystal form M is shown in FIG. 2, and the crystal form M has an endothermic peak at 122.76° C.

(3) TGA Detection

TGA determination was performed by using the crystal form M under the following conditions:

determination was preformed by TA550 from TA Instrument Company, USA, with a heating rate of 10° C./min.

Figure 3:
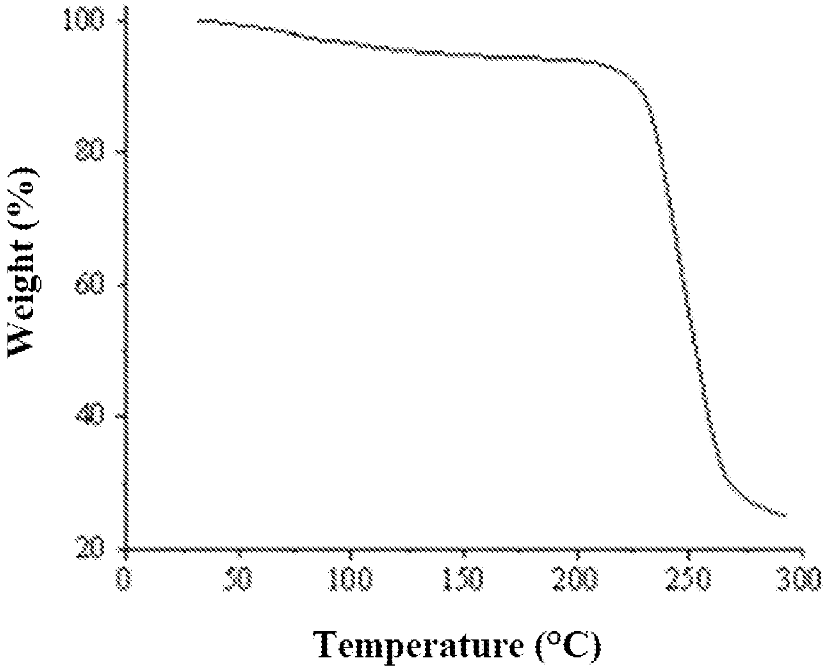
FIG. 3 is a thermo gravimetric analysis curve of the crystal form M in Example 1 according to the present disclosure.

The TGA curve of the crystal form M is shown in FIG. 3, illustrating that the crystal form M was desolvated by 3.2% before 100° C.

Comparative Example 1 Preparation of a Crystal Form CS1

A raw drug of N-[(1,3-dicyclohexylhexahydro-2,4,6-trioxo-5-pyrimidinyl)carbonyl]glycine (i.e., a raw drug of a compound of a formula (I)) was prepared according to the prior art, e.g., according to the method disclosed in CN101505752B. The raw drug of N-[(1,3-dicyclohexylhexahydro-2,4,6-trioxo-5-pyrimidinyl)carbonyl]glycine in this comparative example was prepared by Shanghai Haoyuan Biopharmaceutical Technology Co., Ltd. by repeating the method disclosed in the prior art CN101505752B. The raw drug of the compound of the formula (I) was subjected to X-ray powder diffraction with the following measurement conditions:

determination was performed by using Cu-Kα under a voltage of 40 KV, and a current of 40 mA at a test angle of 3-45°, a step length of 0.02°, an exposure time of 0.2 S, and a light tube slit width of 1 mm by using a Dtex detector with a slit width of 2.7 mm and a Germany BRUKER D8 DISCOVER type X-ray powder diffractometer.

Figure 4:
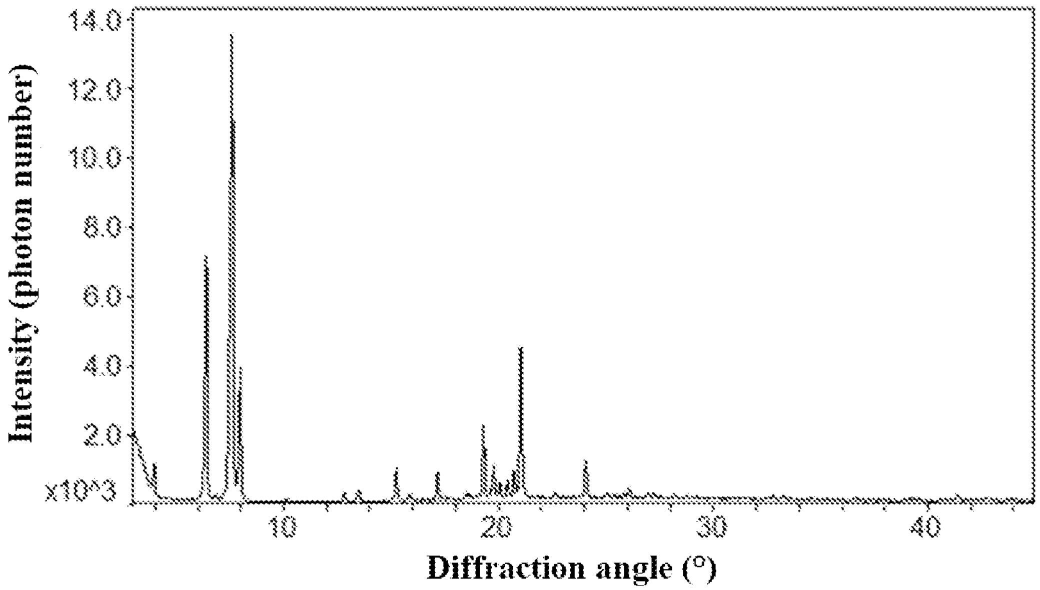
FIG. 4 is an X-ray diffraction pattern of a crystal form CS1 in Comparative Example 1 according to the present disclosure.

An XRPD pattern of the raw drug of the compound of the formula (I) as described above is shown in FIG. 4, and the specific X-ray diffraction positions and intensities are shown in Table 2. From FIG. 4 and Table 2, it can be seen that the raw drug of the compound of the formula (I) is substantially consistent with the crystal form CS1 in the patent literature (WO2019052133), and the raw drug of the compound was named as the crystal form CS1.

TABLE 2

| X-ray diffraction results of the crystal form CS1 | | |
|---|---|---|
| 2θ (±0.2°) | d | I % |
| 3.959 | 22.3005 | 8.1 |
| 6.388 | 13.8252 | 51.9 |
| 7.586 | 11.6447 | 100 |
| 7.967 | 11.0882 | 28.6 |
| 12.833 | 6.8927 | 2 |
| 13.495 | 6.5557 | 2.6 |
| 15.233 | 5.8116 | 7.1 |
| 15.849 | 5.587 | 1.5 |
| 17.167 | 5.1609 | 6 |
| 19.304 | 4.5941 | 15.5 |
| 19.783 | 4.4841 | 6.9 |
| 20.058 | 4.4232 | 3.1 |
| 20.42 | 4.3456 | 3.5 |
| 20.725 | 4.2824 | 6 |
| 21.039 | 4.219 | 32.1 |
| 24.056 | 3.6964 | 8 |
| 26.093 | 3.4122 | 2.1 |

(2) DSC Determination

DSC determination was performed by using the crystal form CS1 under the following conditions:

determination was performed by a TA250 differential scanning calorimeter from TA Instrument Company, USA, with nitrogen protection and a heating rate of 10° C./min.

Figure 5:
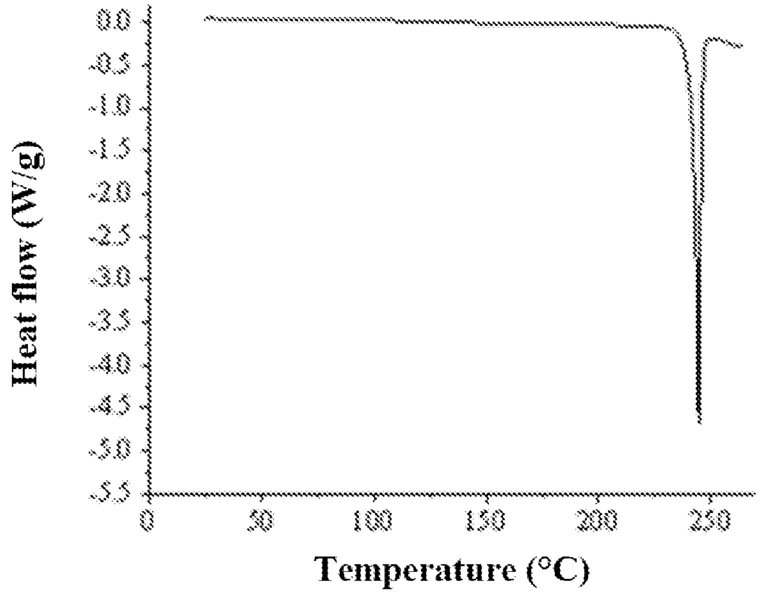
FIG. 5 is a differential scanning calorimetry curve of the crystal form CS1 in Comparative Example 1 according to the present disclosure.

The DSC pattern of the crystal form CS1 is shown in FIG. 5, and the crystal form CS1 has an absorption peak at 244.50° C.

(3) TGA Detection

TGA determination was performed by using the crystal form CS1 under the following conditions:

determination was performed by TA550 from TA Instrument Company, USA, with a heating rate of 10° C./min.

Figure 6:
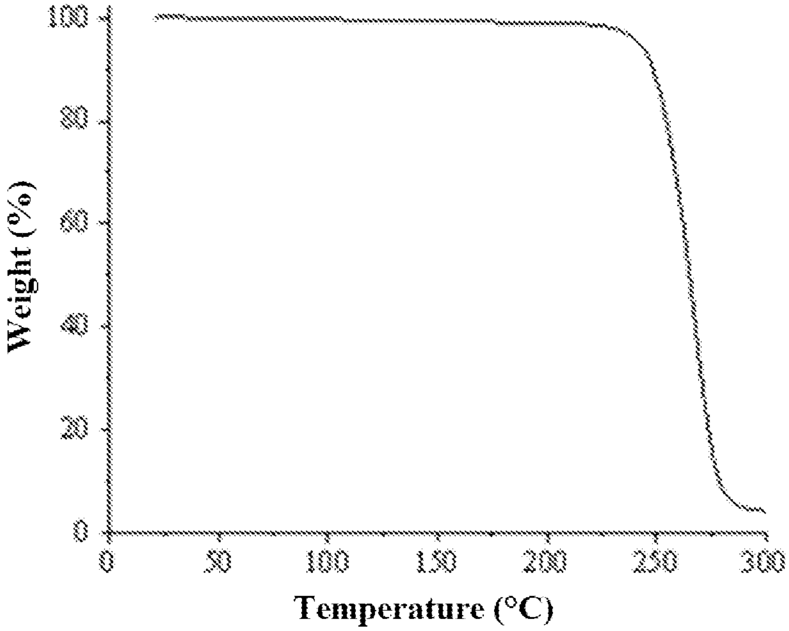
FIG. 6 is a thermo gravimetric analysis curve of the crystal form CS1 in Comparative Example 1 according to the present disclosure.

The TGA curve of the crystal form CS1 is shown in FIG. 6, illustrating that the crystal form CS1 was desolvated by 0.3% before 100° C.

Comparative Example 2 Preparation of a Crystal Form CS9

60 mg of a crystal form CS1 was weighed in a sample vial, 15 ml of 4-methyl-2-pentanone was added and the mixture was heated to 40° C. to dissolve the crystal form CS1 completely. 20 MHz of 85% rated power was used to sonicate for 10 min, then 200 μl of a 0.1 mol/L aqueous sodium dodecyl benzenesulfonate solution was added, and the mixture was heated to 50° C., stirred for 48 h, concentrated, and filtered to obtain a solid. 10 ml of water was added into the solid, and the mixture was continued to be stirred at 50° C. for 30 min and filtered to obtain an off-white solid. XRPD test was performed on the off-white solid, showing a crystalline structure, which was substantially consistent with the crystal form CS9 in the literature (WO2019052133), and the off-white solid was named as the crystal form CS9 below. The crystal form CS9 was characterized by differential scanning calorimetry (DSC) and thermogravimetric analysis (TGA), respectively.

(1) X-Ray Powder Diffraction (XRPD)

X-ray powder diffraction was performed by using the crystal form CS9 with the following measurement conditions:

determination was performed by using Cu-Kα under a voltage of 40 KV, and a current of 40 mA at a test angle of 3-45°, a step length of 0.02°, an exposure time of 0.2 S, and a light tube slit width of 1 mm by using a Dtex detector with a slit width of 2.7 mm and a Germany BRUKER D8 DISCOVER type X-ray powder diffractometer.

Figure 7:
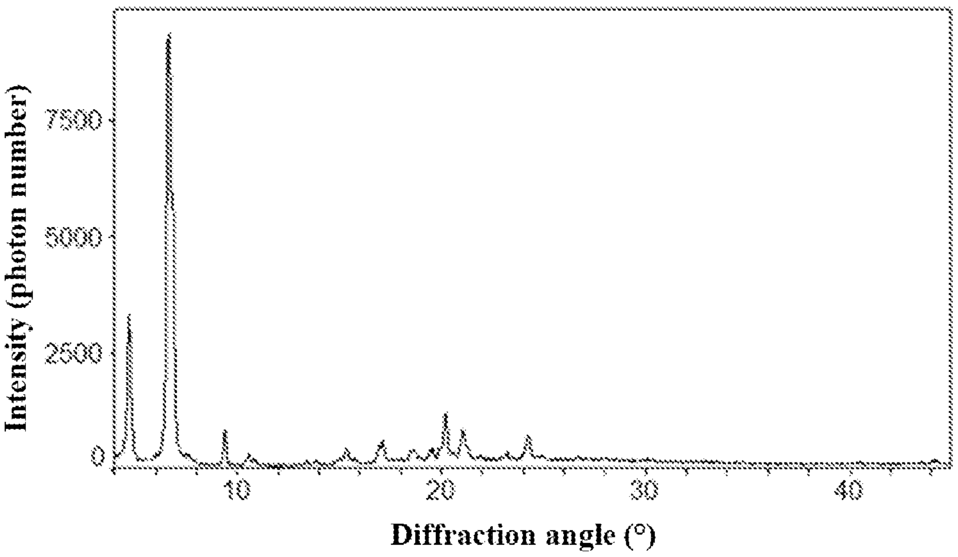
FIG. 7 is an X-ray diffraction pattern of a crystal form CS9 in Comparative Example 2 according to the present disclosure.

The XRPD pattern of the above crystal form CS9 is shown in FIG. 7. The specific X-ray diffraction positions of the crystal form CS9 are shown in Table 3.

TABLE 3

| X-ray diffraction results of the crystal form CS9 | | |
|---|---|---|
| 2θ (±0.2°) | d (Å) | I % |
| 4.695 | 18.8041 | 33.8 |
| 6.616 | 13.3499 | 100 |
| 9.389 | 9.4121 | 8.1 |
| 10.583 | 8.352 | 2.8 |
| 13.383 | 6.6104 | 1.3 |
| 13.816 | 6.4042 | 1.1 |
| 15.316 | 5.7804 | 3.6 |
| 17.13 | 5.1722 | 5.2 |
| 17.625 | 5.028 | 0.8 |
| 18.528 | 4.7848 | 2.6 |
| 19.509 | 4.5465 | 2.2 |
| 20.202 | 4.3919 | 10.2 |
| 21.044 | 4.2182 | 6.2 |
| 23.211 | 3.829 | 1.6 |
| 24.235 | 3.6694 | 5.5 |

(2) DSC Determination

DSC determination was performed by using the crystal form CS9 under the following conditions:

determination was performed by a TA250 differential scanning calorimeter from TA Instrument Company, USA, with nitrogen protection and a heating rate of 10° C./min.

Figure 8:
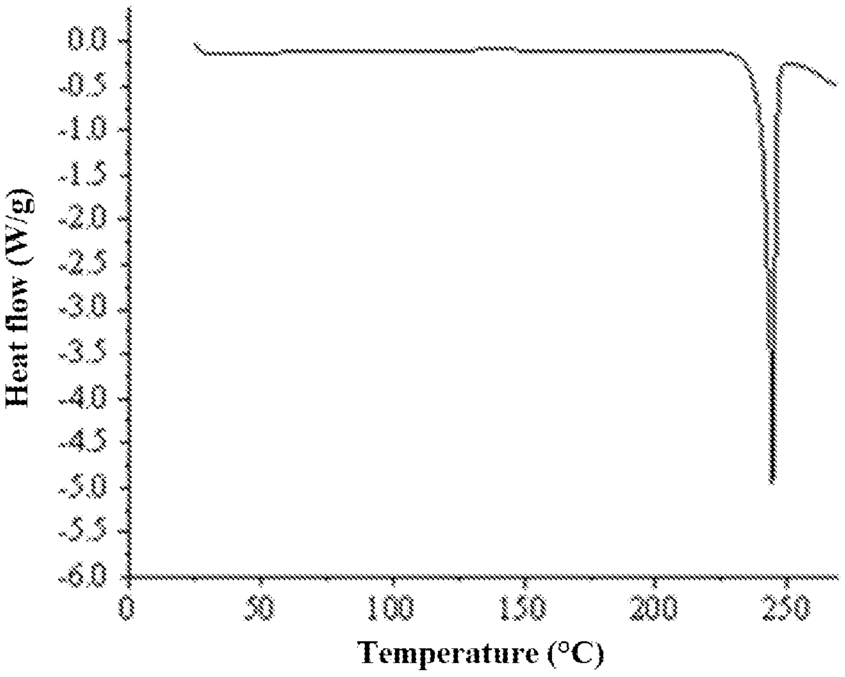
FIG. 8 is a differential scanning calorimetry curve of the crystal form CS9 in Comparative Example 2 according to the present disclosure.

The DSC pattern of the crystal form CS9 is shown in FIG. 8, and the crystal form CS9 has an absorption peak at 244.3° C.

(3) TGA Detection

TGA determination were performed by using the crystal form CS9 under the following conditions:

determination was preformed by TA550 from TA Instrument Company, USA, with a heating rate of 10° C./min.

Figure 9:
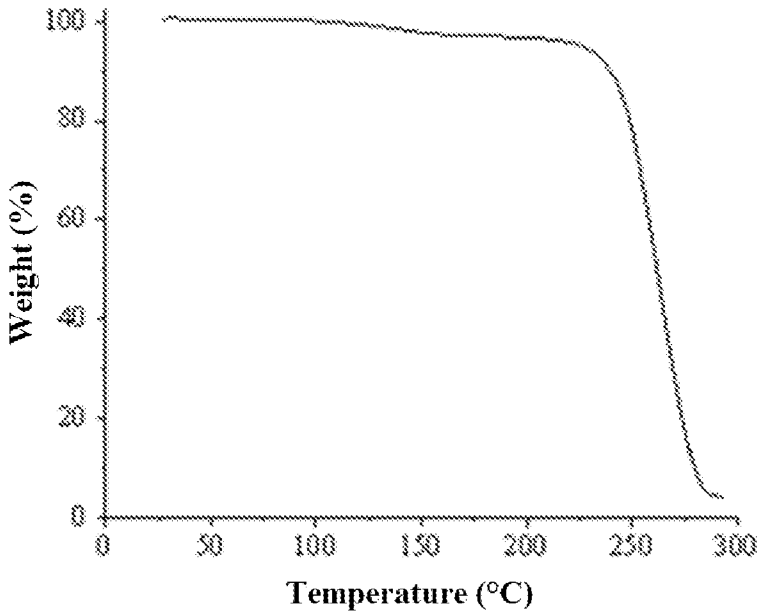
FIG. 9 is a thermo gravimetric analysis curve of the crystal form CS9 in Comparative Example 2 according to the present disclosure.

The TGA curve of the crystal form CS9 is shown in FIG. 9, and shows that the crystal form CS9 was desolvated by 0.08% before 100° C.

Comparative Example 3 Preparation of a Crystal Form K 70 mg of a crystal form CS1 was weighed in a sample vial, 0.5 ml of N,N-dimethylformamide was added and the mixture was heated to 40° C. to dissolve the crystal form CS1 completely. 20 ml of acetonitrile was added, and the mixture was cooled to −15° C. and stirred for 12 h to obtain a white solid precipitate, and filtering and drying were performed to obtain an off-white solid. XRPD test was performed on the off-white solid, showing a crystalline structure, named as a crystal form K. The structure of the prepared crystal form K was then characterized by differential scanning calorimetry (DSC) and thermogravimetric analysis (TGA), respectively.

(1) X-Ray Powder Diffraction (XRPD)

X-ray powder diffraction was performed by using the crystal form K under the following measurement conditions:

determination was performed by using Cu-Kα under a voltage of 40 KV, and a current of 40 mA at a test angle of 3-45°, a step length of 0.02°, an exposure time of 0.2 S, and a light tube slit width of 1 mm by using a Dtex detector with a slit width of 2.7 mm and a Germany BRUKER D8 DISCOVER type X-ray powder diffractometer.

Figure 10:
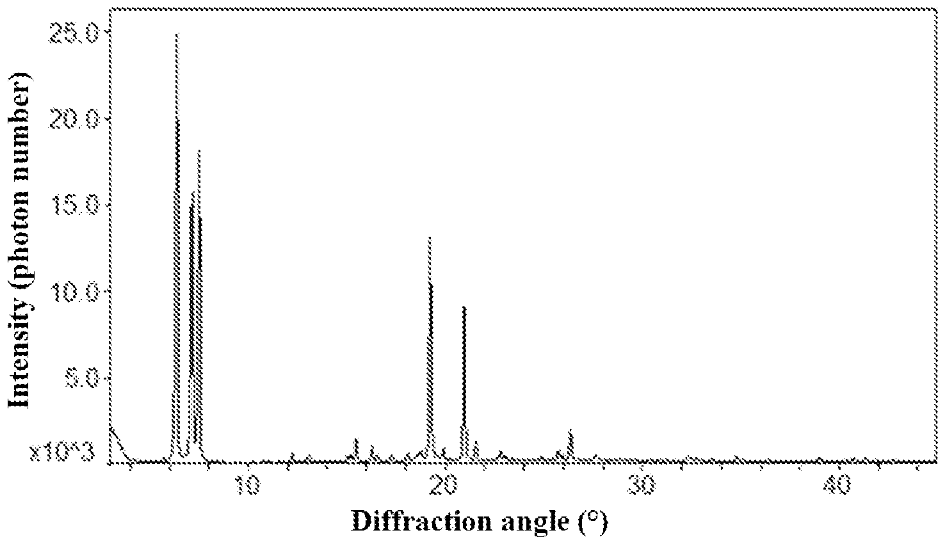
FIG. 10 is an X-ray diffraction pattern of a crystal form K in Comparative Example 3 according to the present disclosure.

An XRPD pattern of the above crystal form K is shown in FIG. 10. The specific X-ray diffraction positions of the crystal form K are shown in Table 4.

TABLE 4

| X-ray diffraction results of the crystal form K | | |
|---|---|---|
| 2θ (±0.2°) | d (Å) | I % |
| 6.37 | 13.8642 | 100 |
| 7.146 | 12.3598 | 62.7 |
| 7.505 | 11.7696 | 72.5 |
| 10.806 | 8.1802 | 0.6 |
| 12.254 | 7.217 | 2.1 |
| 13.075 | 6.7653 | 1.7 |
| 13.495 | 6.5559 | 0.2 |
| 15.469 | 5.7233 | 5.3 |
| 16.291 | 5.4365 | 3.5 |
| 16.549 | 5.3523 | 1.5 |
| 17.267 | 5.1314 | 1.4 |
| 18.086 | 4.9006 | 1.5 |
| 18.781 | 4.7209 | 2.4 |
| 19.225 | 4.613 | 52 |
| 19.887 | 4.4609 | 2.5 |
| 20.958 | 4.2352 | 35.6 |
| 21.56 | 4.1183 | 4.5 |
| 22.819 | 3.8938 | 2 |
| 25.732 | 3.4592 | 2.2 |
| 26.348 | 3.3797 | 7 |

(2) DSC Determination

DSC determination was performed by using the crystal form K under the following conditions:

determination was measured by a TA250 differential scanning calorimeter from TA Instrument Company, USA, with nitrogen protection and a heating rate of 10° C./min.

Figure 11:
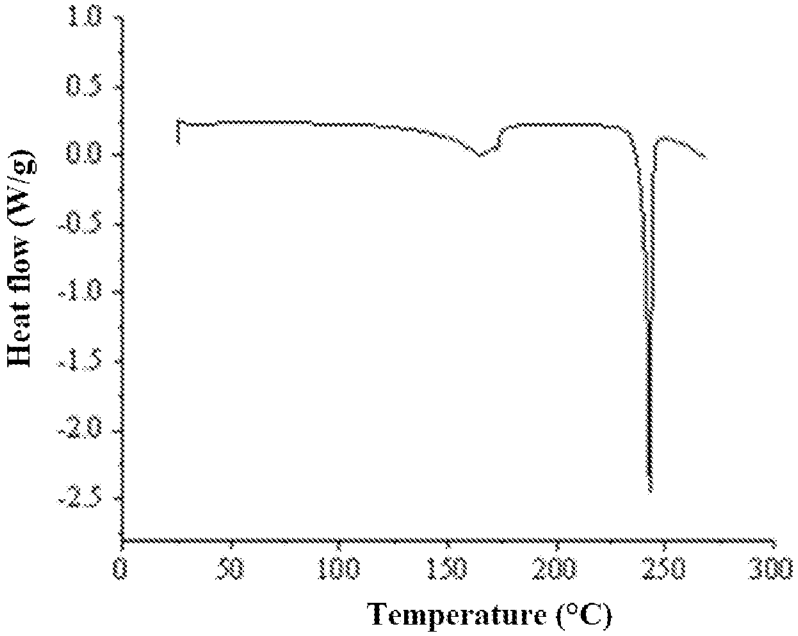
FIG. 11 is a differential scanning calorimetry curve of the crystal form K in Comparative Example 3 according to the present disclosure.

The DSC pattern of the crystal form K is shown in FIG. 11, which shows that the crystal form K has absorption peaks at 165° C. and 243° C.

(3) TGA Detection

TGA determination was performed by using the crystal form K under the following conditions:

determination was performed by TA550 from TA Instrument Company, USA, with a heating rate of 10° C./min.

Figure 12:
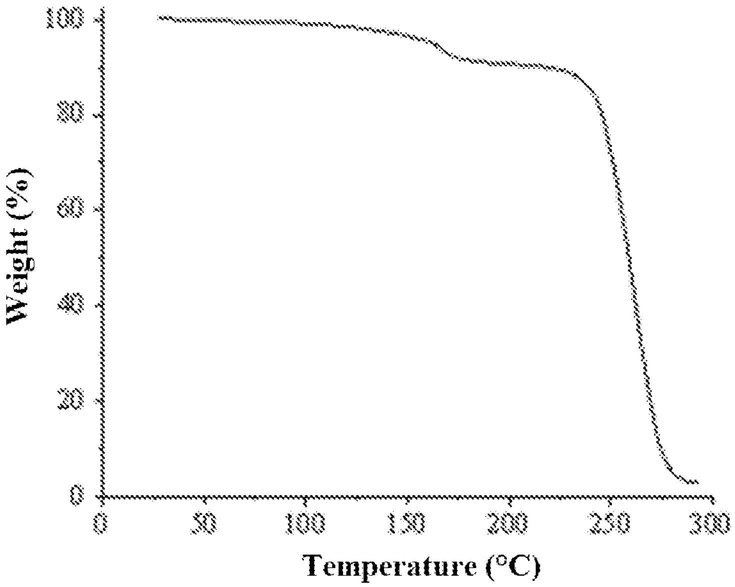
FIG. 12 is a thermo gravimetric analysis curve of the crystal form K in Comparative Example 3 according to the present disclosure.

The TGA pattern of the crystal form K is shown in FIG. 12, and shows that the crystal form K was desolvated by 1.08% before 100° C.

Experimental Example 1 Study on the Solubility of the Crystal Form M

Test product: the crystal form M, crystal form CS1, crystal form CS9 and crystal form K of the compound of the formula (I), preparation methods thereof being respectively shown in Example 1, Comparative example 1, Comparative example 2 and Comparative example 3.

Test method: the saturation solubilities in water of the crystal form M, crystal form CS1, crystal form CS9 and crystal form K of the compound of the formula (I) were determined by respectively taking excess test products, placing the test products in 10 mg sample vials, adding 3 ml of aqueous solution, stirring at room temperature for 12 h, and testing the solubility in water by an HPLC method. The operating conditions of HPLC were as follows:

Instrument: high performance liquid chromatograph (model: Thermo U3000)

Chromatographic column: Agilent C18 column (5 μm, 150 mm×4.6 mm)

Mobile phase composition and gradient elution procedure:

TABLE 5

| Gradient elution procedure | | |
|---|---|---|
| Time (min) | 0.5% aqueous phosphoric acid solution (%) | Acetonitrile (%) |
| 0 | 95 | 5 |
| 3 | 95 | 5 |
| 8 | 5 | 95 |
| 15 | 5 | 95 |

Detection wavelength: 260.4 nm

Flow rate: 1 mL/min

Injection volume: 15 μL

Column temperature: 30° C.

The results are shown in Table 6.

TABLE 6

| Saturation solubility results | |
|---|---|
| Item | Saturation solubility |
| Crystal form M | 42.47 μg/ml |
| Crystal form K | 23.36 μg/ml |
| Crystal form CS1 | 24.48 μg/ml |
| Crystal form CS9 | 19.4 μg/ml |

From the above table, it can be seen that the saturation solubility of the crystal form M is significantly higher compared with those of the crystal form K, the crystal form CS1 and the crystal form CS9.

Experimental Example 2 Study on the Purity of the Crystal Form M

Test product: the crystal form M, crystal form CS1, crystal form CS9 and crystal form K of the compound of the formula (I), preparation methods thereof being respectively shown in Example 1, Comparative example 1, Comparative example 2 and Comparative example 3.

Test method: an HPLC method was adopted, and determination was performed by an external standard method with reference to the method in Appendix VD of the Chinese Pharmacopoeia (2015 edition) by using samples on day 0 as a control.

Operating Conditions of HPLC

Instrument: high performance liquid chromatograph (model: Thermo U3000)

Chromatographic column: Agilent C18 column (5 μm, 150 mm×4.6 mm)

Mobile phase composition and gradient elution procedure:

TABLE 7

| Gradient elution procedure | | |
|---|---|---|
| Time (min) | 0.5% aqueous phosphoric acid solution (%) | Acetonitrile (%) |
| 0 | 95 | 5 |
| 3 | 95 | 5 |
| 8 | 5 | 95 |
| 15 | 5 | 95 |

Detection wavelength: 260.4 nm

Flow rate: 1 mL/min

Injection volume: 15 μL

Column temperature: 30° C.

The results are shown in Table 8.

TABLE 8

| Purity results | | | | |
|---|---|---|---|---|
| | Crystal form M | Crystal form K | Crystal form CS1 | Crystal form CS9 |
| Purity | 99.96% | 99.91% | 99.83% | 99.81% |
| Impurity content | 0.04% | 0.09% | 0.17% | 0.19% |

Compared with that of the crystal form CS1 and the crystal form CS9, the purity of the crystal form M was improved by 0.13% and 0.15%, respectively. The crystal form M of the present disclosure has higher purity and lower impurity content, which can not only improve the safety of a drug for use, but also solve the problem of low activity due to low content.

Experimental Example 3 Study on the Stability of the Crystal Form M

1. Experimental Method

Light stability: samples of the crystal form M, crystal form CS1, crystal form CS9 and crystal form K (prepared in Example 1, Comparative example 1, Comparative example 2 and Comparative example 3, respectively) of the compound of the formula (I) were placed under illumination conditions of 4500 Lux at 25° C. for 10 days, respectively. Samples were taken on Day 5 and Day 10 at fixed time points, respectively, to determine the XRPD patterns of the crystal form M and the crystal form K and the content of N-[(1,3-dicyclohexylhexahydro-2,4,6-trioxo-5-pyrimidinyl)carbonyl]glycine in the crystal form M, the crystal form K, the crystal form CS1 and a crystal form CS9, which were compared with those of samples on day 0.

High temperature stability: samples of the crystal form M, crystal form CS1, crystal form CS9 and crystal form K (prepared in Example 1, Comparative example 1, Comparative example 2 and Comparative example 3, respectively) of the compound of the formula (I) were placed at 60° C. for 10 days, respectively. Samples were taken on Day 5 and Day 10 at fixed time points, respectively, to determine the XRPD patterns of the crystal form M and the crystal form K and the content of N-[(1,3-dicyclohexylhexahydro-2,4,6-trioxo-5-pyrimidinyl)carbonyl] glycine in the crystal form M, the crystal form K, the crystal form CS1 and the crystal form CS9, which were compared with those of samples on day 0.

High humidity stability: samples of the crystal form M, crystal form CS1, crystal form CS9 and crystal form K (prepared in Example 1, Comparative example 1, Comparative example 2 and Comparative example 3, respectively) of the compound of the formula (I) were placed at 40° C. at 75% RH for 10 days, respectively. Samples were taken on Day 5 and Day 10 at fixed time points, respectively, to determine the XRPD patterns of the crystal form M and the crystal form K and the content of N-[(1,3-dicyclohexylhexahydro-2,4,6-trioxo-5-pyrimidinyl)carbonyl] glycine in the crystal form M, the crystal form K, the crystal form CS1 and the crystal form CS9, which were compared with those of samples on day 0.

The specific stability study method can refer to the method in Appendix XI C of Part II of Chinese Pharmacopoeia (2015 edition); the purity was detected by HPLC, and can be determined by an external standard method with reference to the method in Appendix VD of the Chinese Pharmacopoeia (2015 edition) by using samples on day 0 as a control.

Operating Conditions of HPLC

Instrument: high performance liquid chromatograph (model: Thermo U3000)

Chromatographic column: Agilent C18 column (5 μm, 150 mm×4.6 mm)

Mobile phase composition and gradient elution procedure.

TABLE 9

Gradient elution procedure

| Time (min) | 0.5% aqueous phosphoric acid solution (%) | Acetonitrile (%) |
|---|---|---|
| 0 | 95 | 5 |
| 3 | 95 | 5 |
| 8 | 5 | 95 |
| 15 | 5 | 95 |

Detection wavelength: 260.4 nm

Flow rate: 1 mL/min

Injection volume: 15 μL

Column temperature: 30° C.

2. Experimental Results

Figure 13:
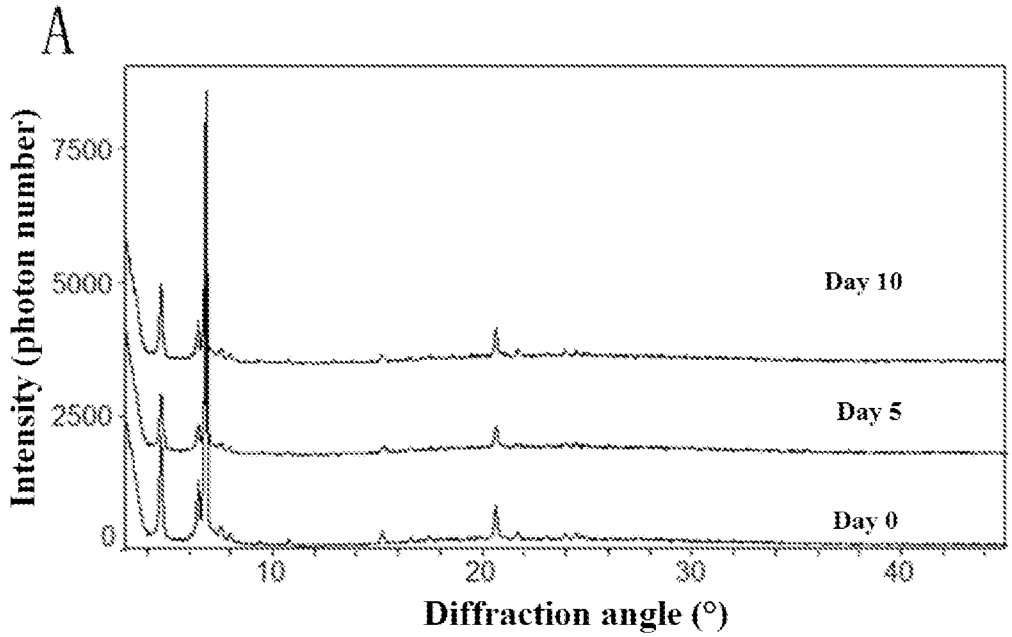
FIG. 13 is a comparative X-ray powder diffraction pattern showing the light stability of a crystal form M and the crystal form K in Experimental Example 3 according to the present disclosure; wherein, A is a comparative X-ray powder diffraction pattern showing the light stability of the crystal form M, and B is a comparative X-ray powder diffraction pattern showing the light stability of the crystal form K.
Figure 13:
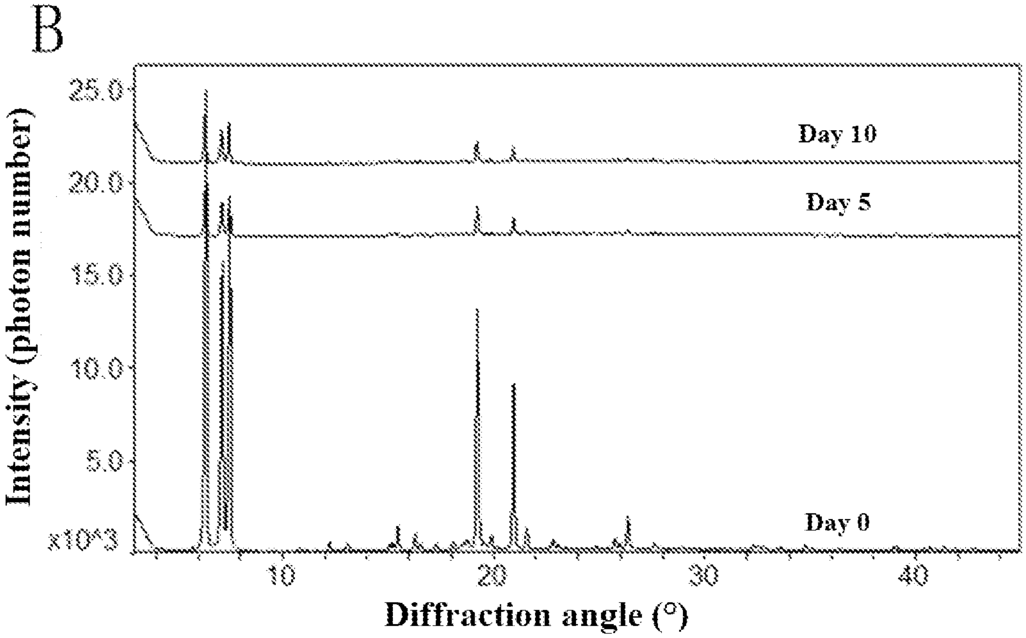
Figure 14:
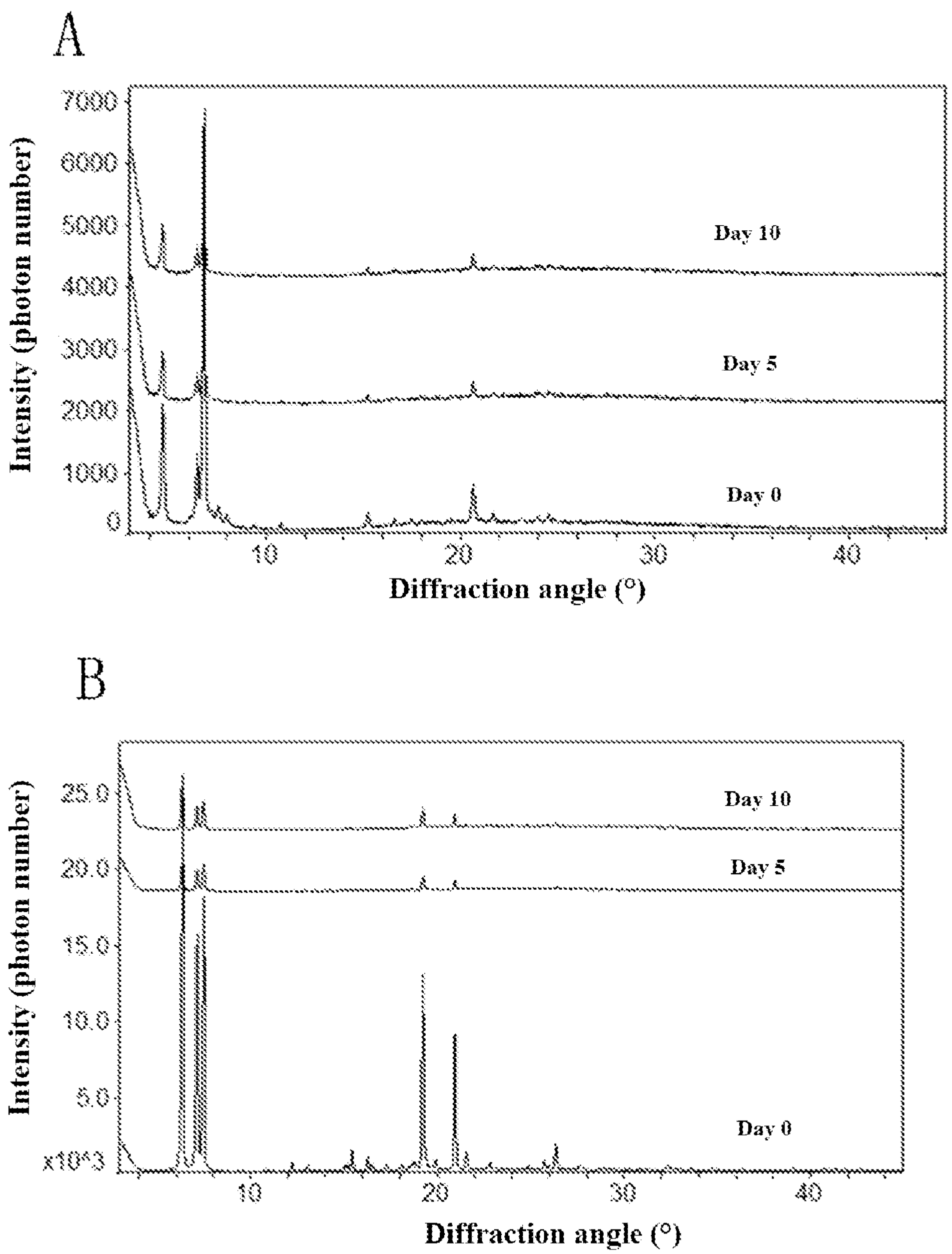
FIG. 14 is a comparative X-ray powder diffraction pattern showing the high temperature stability of the crystal form M and the crystal form K in Experimental Example 3 according to the present disclosure; wherein, A is a comparative X-ray powder diffraction pattern showing the high temperature stability of the crystal form M, and B is a comparative X-ray powder diffraction pattern showing the high temperature stability of the crystal form K.
Figure 15:
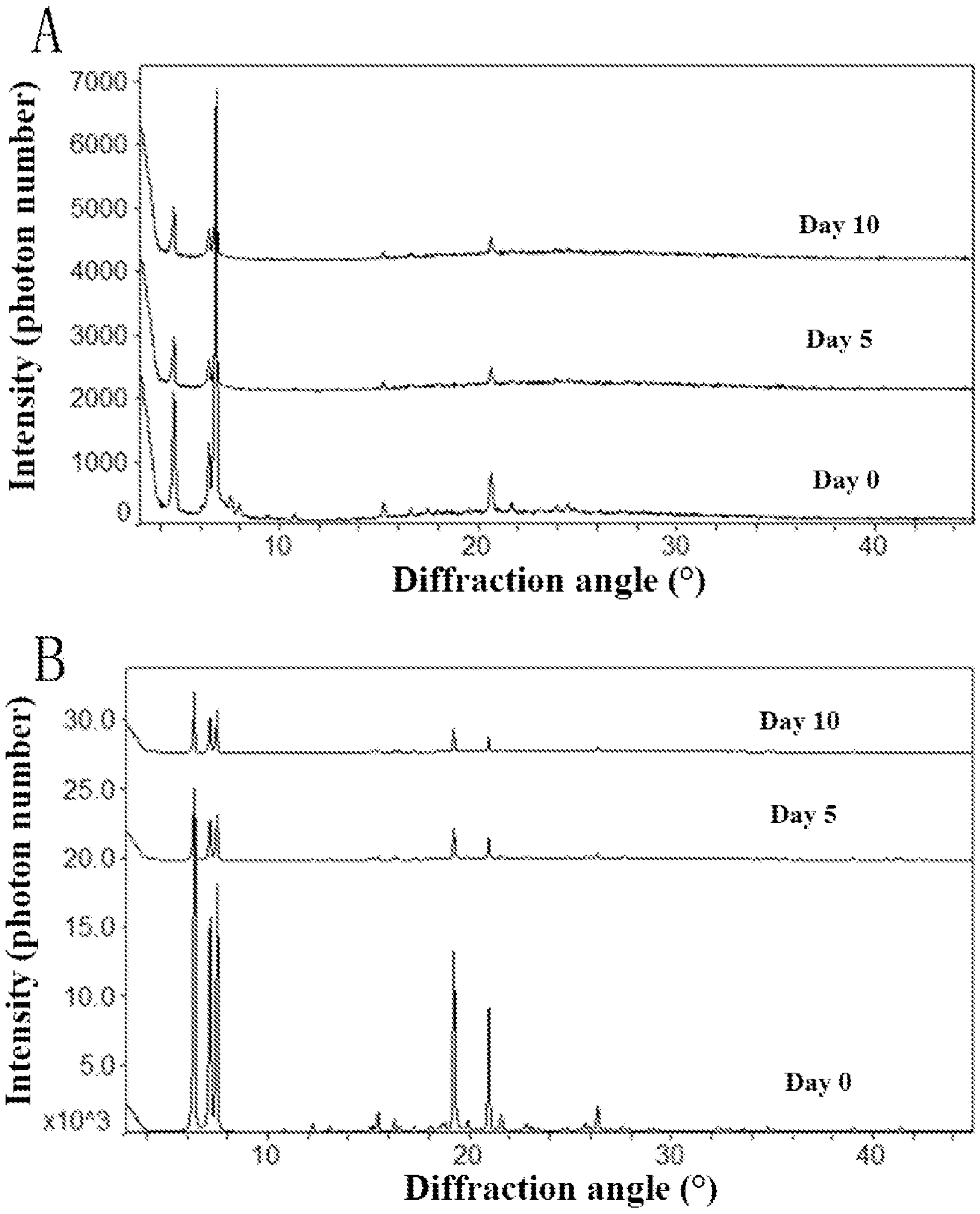
FIG. 15 is a comparative X-ray powder diffraction pattern showing the high humidity stability of the crystal form M and the crystal form K in Experimental Example 3 according to the present disclosure; wherein, A is a comparative X-ray powder diffraction pattern showing the high humidity stability of the crystal form M and B is a comparative X-ray powder diffraction pattern showing the high humidity stability of the crystal form K.

From FIGS. 13-15, it can be seen that the crystal form M and the crystal form K have good stability under strong light (25° C., 4500 Lux), high temperature (60° C.) and high humidity (25° C., 92.5% RH), and no crystalline transformation occurred. The crystal forms M and K provided in the present application have good light stability, high temperature stability, and high humidity stability, and the purity was substantially unchanged during 10 days of placement, indicating that the crystal form M has good stability and is not easily degraded, which can guarantee the preparation of stable formulations.

TABLE 10

Stability study results of the crystal form M

| Conditions | Starting purity (day 0) | Purity on day 10 | Purity change on day 10 |
|---|---|---|---|
| 25° C., 4500 Lux | 99.96% | 99.91% | 0.05% |
| 60° C. | | 99.84% | 0.12% |
| 40° C., 75% RH | | 99.82% | 0.14% |

TABLE 11

Stability study results of the crystal form K

| Conditions | Starting purity (day 0) | Purity on day 10 | Purity change on day 10 |
|---|---|---|---|
| 25° C., 4500 Lux | 99.91% | 99.86% | 0.50% |
| 60° C. | | 99.64% | 0.27% |
| 40° C., 75% RH | | 99.57% | 0.34% |

It is apparent that the foregoing examples are only examples for clear explanation and are not intended to limit the implementations. Other variations or changes may be made in different forms based on the above description for those of ordinary skill in the art. It is not necessary, nor is it possible, to give an exhaustive list of embodiments. The obvious variations or changes derived therefrom are still within the protection scope of the disclosure.

What is claimed is:

1. A crystal form of daprodustat, wherein an X-ray powder diffraction of the crystal form using Cu-Kα radiation has characteristic peaks at 2θ angles of 4.7±0.2°, 6.5±0.2° and 6.8±0.2°.

2. The crystal form of daprodustat according to claim 1, wherein the X-ray powder diffraction of the crystal form using Cu-Kα radiation further has a characteristic peak at 2θ angle of 20.7±0.2°.

3. The crystal form of daprodustat according to claim 1, wherein the X-ray powder diffraction of the crystal form using Cu-Kα radiation further has characteristic peaks at 2θ angles of 7.5±0.2° and 7.9±0.2°.

4. The crystal form of daprodustat according to claim 1, wherein the crystal form has the following X-ray powder diffraction pattern data:

| 2θ (±0.2°) | d (Å) | I % |
|---|---|---|
| 4.7 | 18.9 | 27.7 |
| 6.5 | 13.7 | 15.7 |
| 6.8 | 13.0 | 100. |

5. The crystal form of daprodustat according to claim 1, wherein the crystal form has the following X-ray powder diffraction pattern data:

| 2θ (±0.2°) | d (°A) | I % |
|---|---|---|
| 4.7 | 18.9 | 27.7 |
| 6.5 | 13.7 | 15.7 |
| 6.8 | 13.0 | 100 |
| 7.5 | 11.7 | 4.8 |
| 7.9 | 11.1 | 3.4. |

6. The crystal form of daprodustat according to claim 1, wherein the crystal form has the following X-ray powder diffraction pattern data:

| 2θ (±0.2°) | d (Å) | I % |
|---|---|---|
| 4.68 | 18.88 | 27.7 |
| 6.45 | 13.69 | 15.7 |
| 6.81 | 12.97 | 100 |
| 7.55 | 11.70 | 4.8 |
| 7.95 | 11.11 | 3.4 |
| 10.77 | 8.21 | 1.6 |
| 15.27 | 5.80 | 3.5 |

-continued

| 2θ (±0.2°) | d (Å) | I % |
| --- | --- | --- |
| 16.63 | 5.33 | 1.6 |
| 17.49 | 5.07 | 1.5 |
| 20.67 | 4.30 | 9 |
| 21.67 | 4.09 | 2.2. |

7. The crystal form of daprodustat according to claim 1, wherein the crystal form has an X-ray powder diffraction pattern substantially as shown in FIG. 1.

8. The crystal form of daprodustat according to claim 1, wherein a differential scanning calorimetry curve of the crystal form has an absorption peak at 122.8±2° C.

9. The crystal form of daprodustat according to claim 1, wherein the crystal form has a differential scanning calorimetry curve substantially as shown in FIG. 2.

10. The crystal form of daprodustat according to claim 1, wherein the crystal form has a thermal weight loss of less than 3.2% before 100° C. in a thermo gravimetric analysis curve.

11. The crystal form of daprodustat according to claim 1, wherein the crystal form has a thermo gravimetric analysis curve substantially as shown in FIG. 3.

12. A method for preparing the crystal form of daprodustat according to claim 1, comprising the steps of: dissolving a crystal form CS1 of the daprodustat in n-butanol or isobutanol, adding an aqueous solution of sodium dodecyl benzenesulfonate and concentrating to obtain a solid, adding the solid into water for slurrying, filtering, and drying to obtain the crystal form of daprodustat.

13. A pharmaceutical composition, comprising the crystal form of daprodustat according to claim 1 and a pharmaceutically acceptable excipient.

14. A method for treating anemia, ischemia, or myocardial infarction in a patient in need thereof, comprising administering a pharmaceutically effective dose of the crystal form of daprodustat according to claim 1 or a pharmaceutical composition comprising the crystal form of daprodustat to the patient.

15. The crystal form of daprodustat according to claim 1, wherein the crystal form is crystal form M.

16. The method according to claim 12, wherein the crystal form of daprodustat is crystal form M.

17. The pharmaceutical composition according to claim 13, wherein the crystal form of daprodustat is crystal form M.

18. The method according to claim 14, wherein the crystal form of daprodustat is crystal form M.

* * * * *